United States Patent [19]

Siegle et al.

[11] 3,954,836
[45] May 4, 1976

[54] N-METHYL-N-(BENZENE SULFONIC ACID METHYLAMIDE-N'-SULFENYL)-CARBAMIC ACID ESTERS

[75] Inventors: Peter Siegle, Cologne; Engelbert Kühle, Bergisch-Gladbach; Ingeborg Hammann, Cologne; Wolfgang Behrenz, Overath-Steinenbrueck, all of Germany

[73] Assignee: Bayer Aktiengesellschaft, Leverkusen, Germany

[22] Filed: Oct. 19, 1973

[21] Appl. No.: 408,253

[30] Foreign Application Priority Data
Nov. 7, 1972  Germany............................ 2254359

[52] U.S. Cl. ........................ 260/470; 260/327 M; 260/340.5; 260/340.6; 260/340.7; 260/340.9; 260/465 D; 260/544 C; 260/556 S; 260/566 AE; 424/276; 424/277; 424/278; 424/282; 424/308
[51] Int. Cl.² ................................ C07C 143/78
[58] Field of Search ........................... 260/470

[56] References Cited
UNITED STATES PATENTS
3,084,096  4/1963  Lambrech ................ 260/479 C Primary Examiner—John F. Terapane
Attorney, Agent, or Firm—Burgess, Dinklage & Sprung

[57] ABSTRACT

N-methyl-N-(benzene sulfonic acid methylamide-N'-sulfenyl)-carbamic acid esters of the formula

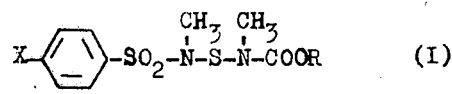

(I)

in which
X is halogen, $C_1$–$C_6$ alkyl or hydrogen, and
R is a phenyl, naphthyl, benzodioxolanyl or indanyl radical optionally carrying at least one alkyl, alkenyl, alkynyl, alkoxy, alkenoxy, alkynoxy, alkylmercapto, alkenylmercapto, alkynylmercapto, dialkylamino, trihalogenomethyl, halogeno, nitro, nitrile, cycloalkyl, formamidino, dioxanyl or dioxolanyl radical; or an oxime radical of the formula

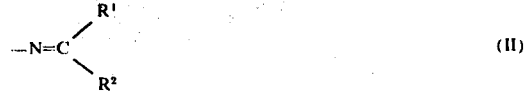

(II)

in which
$R^1$ and $R^2$ each individually is alkyl, alkoxy, alkylthio or alkoxycarbonyl, the alkyl moieties of $R^1$ and $R^2$ optionally being linked to one another, which possess insecticidal and acaricidal properties.

2 Claims, No Drawings

N-METHYL-N-(BENZENE SULFONIC ACID METHYLAMIDE-N'-SULFENYL)-CARBAMIC ACID ESTERS

The present invention relates to and has for its objects the provision of particular new N-methyl-N-(benzene sulfonic acid methylamide-N'-sulfenyl)-carbamic acid esters which are optionally halogen- or alkyl-substituted on the benzene ring of the sulfonamide, which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It has been disclosed in German Published Specifications DAS 1,108,202 and 1,138,277 and Belgian Pat. No. 674,792 that carbamates are effective insecticides. Some of the compounds described therein are commercially available products but have the disadvantage that they are not always entirely satisfactory, particularly if low concentrations are used.

The present invention provides, as new compounds, the N-sulfenylated carbamates of the formula

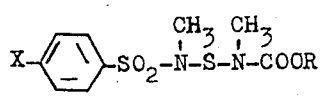

in which
X is halogen, $C_1$–$C_6$ alkyl or hydrogen, and
R is a phenyl, naphthyl, benzodioxolanyl or indanyl radical optionally carrying at least one alkyl, alkenyl, alkynyl, alkoxy, alkenoxy, alkylmercapto, alkenylmercapto, alkynylmercapto, dialkylamino, trihalogenomethyl, halogeno, nitro, nitrile, cycloalkyl, formamidino, dioxanyl or dioxolanyl radical; or an oxime radical of the formula

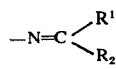

in which
$R^1$ and $R^2$ each individually is alkyl, alkoxy, alkylthio, nitrile or alkoxycarbonyl, the alkyl moieties of $R^1$ and $R^2$ optionally being linked to one another.

The compounds of this invention display strong insecticidal and acaricidal properties.

Preferably the alkyl, alkenyl or alkynyl moieties of the various substituents contain up to about four carbon atoms. More preferably, R is a phenyl, 2-isopropoxyphenyl, 3,5-dimethyl-4-methylmercapto-phenyl, 3-methyl-4-dimethylaminophenyl, 4-nitrophenyl, 2-allyloxyphenyl, 3-sec.-butyl-4-methylphenyl, 4-methyl-3-isopropylphenyl, 2-dimethylaminophenyl, 1-naphthyl, 4-(1,1-dimethylindanyl) or 2,2-dimethylbenzodioxolanyl radical, or an oxime radical derived from acetonoxime, dichloroacetonoxime, malonic acid diethyl ester-oxime, 2-oximino-1,3-dithiolane, 4-methyl-2-oximino-1,3-dithiolane, 4,4-dimethyl-2-oximino-1,3-dithiolane, 4-phenyl-2-oximino-1,3-dithiolane, 2-oximino-1,3-oxathiolane, 2-oximino-1,3-dithiane, 2-oximino-1,3-oxathiane methylthio-hydroxamacetic acid ester or n-butylthio-hydroxamacetic acid ester.

The present invention also provides a process for preparation of an N-sulfenylated carbamate of the general formula (I), in which a carbamic acid fluoride of the general formula

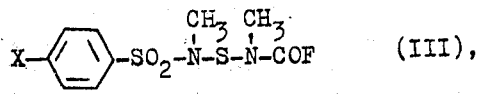

in which
X has the above-mentioned meaning, is reacted with a compound of the general formula

in which
R has the above-mentioned meaning,
if appropriate in the presence of an acid-binding agent and/or of a diluent.

When using 2-oximino-1,3-dithiolane and N-methyl-N-(p-toluenesulfonic acid methylamide-N'-sulfenyl)-carbamic acid fluoride as the starting materials, the course of the reaction can be represented by the following equation:

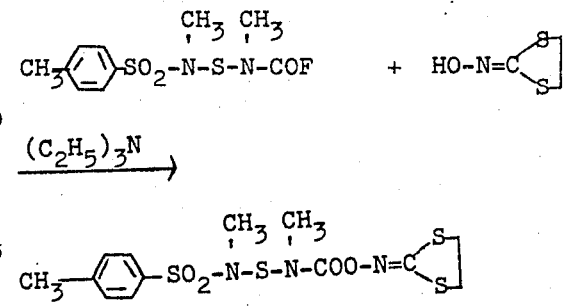

The phenols and oximes that may be employed in the preparative process are known from the literature.

The substituted carbamic acid fluorides required may be prepared by reacting the sodium salt of the appropriate arylsulfonic and methylamide with sulfur dichloride. The disulfide thus obtained is split with chlorine to give the sulfenic acid chloride and the latter is reacted with N-methyl-carbamic acid fluoride. This method of synthesis is represented by the following equation.

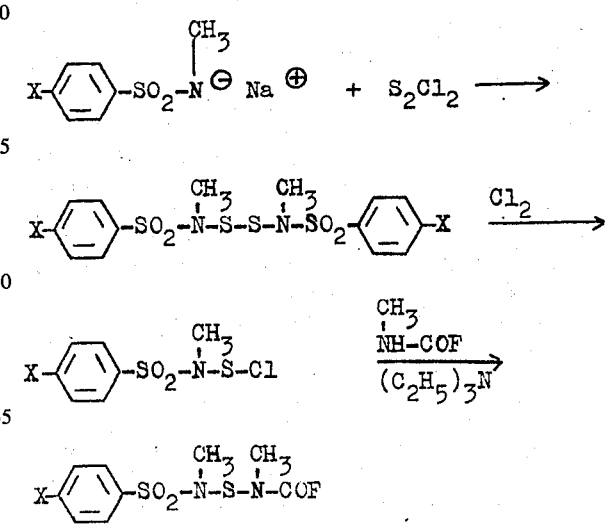

Possible diluents are all inert organic solvents, especially ethers, such as diethyl ether, tetrahydrofuran and dioxane, hydrocarbons, such as benzene, and chlorinated hydrocarbons, such as chloroform and chlorobenzene.

In order to bind the hydrogen fluoride produced in the reaction, a tertiary organic base, for example triethylamine, is preferably added to the reaction mixture.

The reaction temperatures can be varied over a fairly wide range; in general, the reaction is carried out at about 0° to 100°C, preferably at about 20° to 40°C.

Equimolar amounts of the reactants are preferably used in carrying out the process according to this invention.

The active compounds according to the present invention, while having a low toxicity to warm-blooded animals, display strong insecticidal properties and acaricidal properties and can therefore be used with good success for combating harmful sucking and biting insects and mites.

To the sucking insects there belong, in the main, aphids (Aphidae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addtion, scales and mealybugs (Coccina), for example the oleander scale (*Aspidiotus hederae*) and the soft scale (*Lecanium hesperidum*) as well as the grape mealybug (*Pseudococcus maritimus*); thrips (*Thysanoptera*), such as Hercinothrips femoralis, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

Also to be classed with the bitting insects are beetles (Coleoptera), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes spec.*) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia manderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acari) there are classed, in particular, the spider mites (Tetranychidae) such as the two-spotted spider mite (*Tetranychus urticae*) and the European red mite (*Paratetranychus pilosus = Phanonychus ulmi*), gall mites, for example the blackcurrent gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the present compounds are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicle such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaoline, clays, alimina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or rodenticides, fungicides, bactericides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

Phaedon larvae test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) were sprayed with the preparation of the active compound until dripping wet and were then infested with mustard beetle larvae (*Phaedon cochleariae*).

After the specified periods of time. the degree of destruction was determined in %. 100% means that all of the beetle larvae were killed whereas 0% means that none of the beetle larvae were killed.

The active compounds, the concentrations of the active compounds, the evaluation times and the results can be seen from the following table:

Table 1

(insects which are harmful to plants)
(*Phaedon* larvae test)

| Active compounds | | Active compound concentration in % | Degree of destruction in % after 3 days |
|---|---|---|---|
| 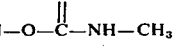 (known) | (A) | 0.1<br>0.01 | 100<br>0 |
|  (known) | (B) | 0.1<br>0.01 | 100<br>0 |
|  | (21) | 0.1<br>0.01 | 100<br>100 |
|  | (12a) | 0.1<br>0.01<br>0.001 | 100<br>100<br>30 |
|  | (15) | 0.1<br>0.01 | 100<br>100 |
|  | (18) | 0.1<br>0.01 | 100<br>100 |
|  | (16) | 0.1<br>0.01 | 100<br>100 |

EXAMPLE 2

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*), which had been heavily infested with peach aphids (*Myzus persicae*), were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 2

(insects which are harmful to plants)
*Myzus* test

| Active compounds | | Active compound concentration in % | Degree of destruction in % after 1 day |
|---|---|---|---|
| (CH₃)₂N-C₆H₃(CH₃)-O-C(=O)-NH-CH₃ (known) | (C) | 0.1<br>0.01 | 98<br>20 |
| naphthyl-O-C(=O)-NH-CH₃ (known) | (D) | 0.1<br>0.01 | 80<br>0 |
| C₆H₅-SO₂-N(CH₃)-S-N(CH₃)-COO-N=C(CH₃)(SCH₃) | (14) | 0.1<br>0.01 | 100<br>100 |
| Cl-C₆H₄-SO₂-N(CH₃)-S-N(CH₃)-COO-N=C(CH₃)(SCH₃) | (23) | 0.1<br>0.01 | 100<br>80 |
| C₆H₅-SO₂-N(CH₃)-S-N(CH₃)-COO-N=C(S-S cyclic) | (17) | 0.1<br>0.01 | 100<br>100 |
| CH₃-C₆H₄-SO₂-N(CH₃)-S-N(CH₃)-COO-N=C(CH₃)(SCH₃) | (6) | 0.1<br>0.01 | 100<br>70 |
| C₆H₅-SO₂-N(CH₃)-S-N(CH₃)-COO-(benzodioxol-C(CH₃)₂) | (18) | 0.1<br>0.01 | 100<br>50 |

EXAMPLE 3

Tetranychus test (resistant)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These beans plants were heavily infested with the two-spotted spider mite (*Tetranychus urticae*) in all stages of development.

After the specified periods of time, the effectiveness of the preparation of active compound was determined by counting the dead mites. The degree of destruction thus obtained is exposed as a percentage: 100% means that all the spider mites were killed whereas 0% means that none of the spider mites were killed.

The active compounds, the concentrations of the active compounds, the evaluation times and the results can be seen from the following table:

Table 3

(mites which are harmful to plants)
*Tetranychus* test (resistant)

| Active compounds | | Active compound concentration in % | Degree of destruction in % after 2 days |
|---|---|---|---|
|  (known) | (B) | 0.1 | 0 |
|  (known) | (D) | 0.1 | 0 |
|  | (14) | 0.1 | 90 |
|  | (23) | 0.1 | 98 |

EXAMPLE 4

Residual test

Test insects: Musca domestica
Wettable powder base consisting of:
3% sodium diisobutylnaphthalene-1-sulfonate
6% sulfite waste liquor, partially condensed with aniline
40% highly dispersed silicic acid (containing CaO)
51% colloidal kaolin.

To produce a suitable preparation of the active compound, 1 part by weight of the active compound was intimately mixed with 9 parts by weight of the wettable powder base. The spray powder thus obtained was suspended in 90 parts of water.

The suspension of the active compound was sprayed, in an amount of 1 g of the active compound per m$^2$, on to substrates consisting of different materials.

The sprayed coatings were, at specific intervals of time, tested for their biological activity.

For this purpose, the test insects were placed on the treated substrates. There was put over the test insects a squat cylinder which was closed at its upper end with a wire mesh in order to prevent the insects from escaping. After the insects had spent 8 hours on the substrate, the knock-down effect was determined as a percentage.

The active compounds, the nature of the test substrates, and the results, can be seen from the following table:

Table 4

| Active compounds | Test substrates | Test animals | Destruction of the test animals in % Age of the residual coatings in weeks | | | | | | | | |
|---|---|---|---|---|---|---|---|---|---|---|---|
| | | | 1 | 2 | 4 | 6 | 8 | 12 | 16 | 20 | 24 |
| (B) (known) | Clay | Musca | 100 | 100 | 100 | 100 | 90 | 30 | 40 | 0 | — |
| | Plywood | domestica | 100 | 100 | 100 | 100 | 100 | 50 | 0 | — | — |
| (1) | Clay | Musca | 100 | 100 | 100 | 100 | 100 | 100 | 100 | 100 | 100 |
| | Plywood | domestica | 100 | 100 | 100 | 100 | 100 | 100 | 100 | 100 | 70 |

EXAMPLE 5

Critical concentration test/soil insects

Test insect: Tenebrio molitor larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance; only the amount by weight of active compound per unit volume of soil, which is given in ppm (for example mg/l), was decisive. The soil as filled into pots and the pots were left to stand at room temperature. After 24 hours, the test insects were introduced into the treated soil and after a further 48 hours the degree of effectiveness of the active compound was determined in % by counting the dead and live test insects. The degree of destruction was 100% if all test insects were killed and was 0% if just as many test insects were still alive as in the case of the control.

The active compounds, the amounts used and the results can be seen from the table which follows:

Table 5

Soil insecticides
*Tenebrio molitor* in the soil

| Active compound (structure) | Active compound concentration in ppm: | 80 | 60 | 40 | 20 | 10 |
|---|---|---|---|---|---|---|
| [structure with phenyl-SO$_2$-N(CH$_3$)-S-N(CH$_3$)-COO-N=C(CH$_3$)(SCH$_3$)] | (14) | 100 | 100 | 100 | 98 | 50 |
| [Cl-phenyl-SO$_2$-N(CH$_3$)-S-N(CH$_3$)-COO-N=C(CH$_3$)(SCH$_3$)] | (23) | 100 | 100 | 100 | 100 | 90 |
| [CH$_3$-phenyl-SO$_2$-N(CH$_3$)-S-N(CH$_3$)-COO-N=C(CH$_3$)(SCH$_3$)] | (6) | 100 | 100 | 100 | 98 | 30 |
| [CH$_3$-phenyl-SO$_2$-N(CH$_3$)-S-N(CH$_3$)-COO-N=C(CH$_3$)(S-C$_4$H$_9$(n))] | (7) | 100 | 100 | 100 | 95 | 20 |
| [phenyl-SO$_2$=N-S-N-COO-N=C(dithiolane)] | (17) | 100 | 100 | 100 | 98 | 30 |
| [(CH$_3$)$_2$N-phenyl(CH$_3$)-O-C(=O)-NH-CH$_3$] (known) | (C) | 100 | 50 | 0 | | |
| [phenyl(O-CH(CH$_3$)$_2$)-O-C(=O)-NH-CH$_3$] (known) | (B) | 100 | 50 | 0 | | |

The process of the present invention is illustrated in the following preparative Examples.

EXAMPLE 6

Preparation of the carbamic acid fluorides used as the starting materials.

a. Bis-(p-toluenesulfonic acid-methylamido)-disulphide

A solution of 34 g (0.25 mole) of S$_2$Cl$_2$ in 40 ml of anhydrous toluene was slowly added dropwise to a suspension of 104 g (0.5 mole) of the sodium salt of p-toluenesulfonic acid methylamide in 300 ml of anhydrous toluene. The reaction was exothermic and after some time the solution became clear. After stirring for a further 4 hours at 90°C the mixture was cooled to 0°C, the sodium chloride was filtered off and the yellow solution was concentrated.

The oily residue could be recrystallized from methanol. Yield: 80 g (75%); melting point 105°C.

25.1 g (0.1 mole) of the sulfenic acid chloride, ob-

The product could be employed without further purification for the subsequent chlorinating decomposition.
b. (p-Toluene sulfonic acid methylamide)-N-sulfenic acid chloride 413 g of the crude disulfide of (a) were suspended in 1 liter of carbon tetrachloride. Chlorine was then passed in until a clear yellow-red solution was produced. The exothermic reaction was kept below 30°C by slight cooling. The mixture was stirred for a further 2 hours at room temperature and thereafter the solvent was distilled off. The solid residue was recrystallized from benzene/petroleum ether. Yield: 398 g of light yellow crystals; melting point 67°C.

c. Methyl-N-(p-toluenesulfonic acid methylamide-N'-sulfenyl)-carbamic acid fluoride

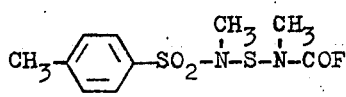

tained according to (b), and 7.7 g (0.1 mole) of N-methylcarbamic acid fluoride were dissolved in 300 ml of benzene. 11 g of triethylamine were added dropwise at room temperature, while stirring. After stirring for a further 2 hours at 40°C, the organic phase was repeatedly extracted by shaking with cold water and was dried with $Na_2SO_4$.

The residue after concentration was recrystallized from cyclohexane. Yield: 24 g (82%); melting point 78°–79°C. 1.4. The following were obtained by procedures analogous to those above:

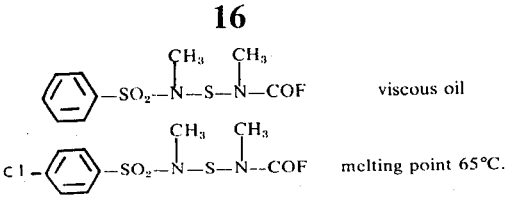

viscous oil melting point 65°C.

EXAMPLE 7

Preparation of the compounds according to the invention

N-Methyl-N-(p-toluenesulfonic acid methylamide-N'-sulfenyl)-carbamic acid o-isopropoxyphenyl ester

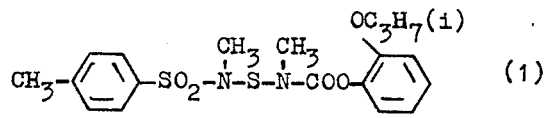

6 g of triethylamine were added dropwise at room temperature to a solution of 14.6 g (0.05 mole) of the carbamic acid fluoride, obtained according to Example 6 (c), and 7.6 g (0.05 mole) of o-isopropoxyphenol in 100 ml of benzene. After stirring for 2 hours at 60°C, the mixture was repeatedly washed with water and the organic phase was then dried with $Na_2SO_4$.

Yield: 15 g of a brown oil (72%); $n_D^{20} = 1.5570$.

The following compounds were prepared by procedures analogous to that described above.

| Compound No. | Formula | Physical properties |
|---|---|---|
| (2) | CH₃—⟨⟩—SO₂—N(CH₃)—S—N(CH₃)—COO—⟨⟩(O-CH₂-C≡CH) | $n_D^{20} = 1.5542$ |
| (3) | CH₃—⟨⟩—SO₂—N(CH₃)—S—N(CH₃)—COO—⟨⟩ (with CH₃/CH₃ dioxolane substituent) | $n_D^{20} = 1.5564$ |
| (4) | CH₃—⟨⟩—SO₂—N(CH₃)—S—N(CH₃)—COO—⟨⟩(C(CH₃)₃) | $n_D^{20} = 1.5352$ |
| (5) | CH₃—⟨⟩—SO₂—N(CH₃)—S—N(CH₃)—COO—N=C(COOC₂H₅)(COOC₂H₅) | $n_D^{20} = 1.5192$ |
| (6) | CH₃—⟨⟩—SO₂—N(CH₃)—S—N(CH₃)—COO—N=C(CH₃)(SCH₃) | melting point 93°C (recrystallized from benzene/petroleum ether) |
| (7) | CH₃—⟨⟩—SO₂—N(CH₃)—S—N(CH₃)—COO—N=C(CH₃)(S-C₄H₉(n)) | melting point 85°C (recrystallized from benzene/petroleum ether) |

-continued

| Compound No. | Formula | Physical properties |
|---|---|---|
| (8) | 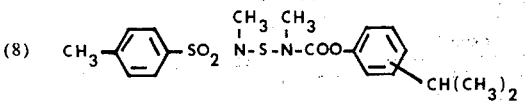 | $n_D^{20} = 1.5553$ | meta: para = 60:40 mixture

| (9) | 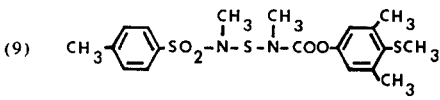 | $n_D^{20} = 1.5790$ |
| (10) | 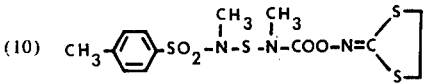 | melting point 122°C (recrystallized from ethanol) |
| (11) | 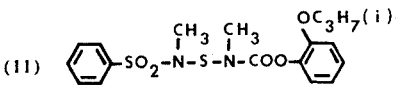 | $n_D^{20} = 1.5583$ |
| (12) | 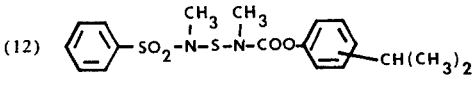 | $n_D^{20} = 1.5590$ | meta: para = 60:40 mixture

| (13) | 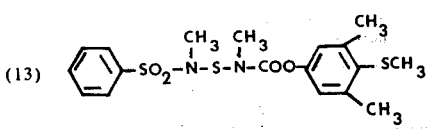 | $n_D^{20} = 1.5815$ |
| (14) | 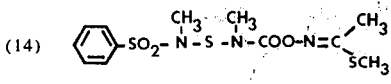 | $n_D^{20} = 1.5698$ |
| (15) | 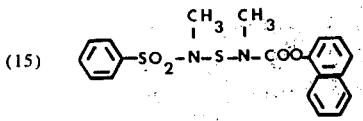 | viscous oil |
| (16) | 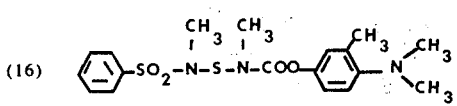 | $n_D^{20} = 1.5755$ |
| (17) | 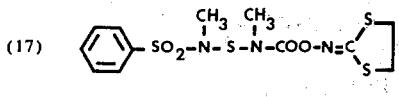 | melting point 120°C (decomposition) (recrystallized from benzene/carbon tetrachloride/ether) |
| (18) | 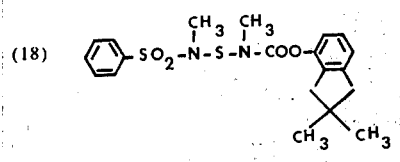 | $n_D^{20} = 1.5620$ |
| (19) | 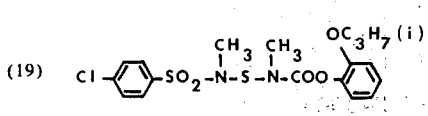 | melting point 72°C (recrystallized from benzene/petroleum ether) |

| Compound No. | Formula | Physical properties |
|---|---|---|
| (20) | Cl-C6H4-SO2-N(CH3)-S-N(CH3)-COO-[2,6-(CH3)2-4-SCH3-C6H2] | melting point 115°C (decomposition) (recrystallized from benzene/petroleum ether) |
| (21) | Cl-C6H4-SO2-N(CH3)-S-N(CH3)-COO-[2-CH3-4-N(CH3)2-C6H3] | $n_d^{20} = 1.5790$ |
| (22) | Cl-C6H4-SO2-N(CH3)-S-N(CH3)-COO-C6H4-CH(CH3)2 | $n_D^{20} = 1.5605$ | meta:para = 60:40 mixture

| (23) | Cl-C6H4-SO2-N(CH3)-S-N(CH3)-COO-N=C(CH3)(SCH3) | $n_D^{20} = 1.5773$ |
| (24) | Cl-C6H4-SO2-N(CH3)-S-N(CH3)-COO-naphthyl | melting point 120°C (decomposition) (recrystallized from benzene/petroleum ether) |

Other compounds which may similarly be prepared include:

$CH_3$-C6H4-SO2-N(CH3)-S-N(CH3)-COO-[indanyl-(CH3)2]  (25)

C6H5-SO2-N(CH3)-S-N(CH3)-COO-C6H4-CH2-CH=CH2  (26)

C6H5-SO2-N(CH3)-S-N(CH3)-COO-C6H4-CH2-C≡CH  (27)

C6H5-SO2-N(CH3)-S-N(CH3)-COO-C6H4-O-CH2-CH=CH2  (28)

$CH_3$-C6H4-SO2-N(CH3)-S-N(CH3)-COO-C6H4-S-CH2-CH=CH2  (29)

C6H5-SO2-N(CH3)-S-N(CH3)-COO-C6H4-S-CH2-C≡CH  (30)

Cl-C6H4-SO2-N(CH3)-S-N(CH3)-COO-C6H4-CF3  (31)

C6H5-SO2-N(CH3)-S-N(CH3)-COO-C6H4-Br  (32)

Cl-C6H4-SO2-N(CH3)-S-N(CH3)-COO-C6H4-NO2  (33)

C6H5-SO2-N(CH3)-S-N(CH3)-COO-C6H4-CN  (34)

C6H5-SO2-N(CH3)-S-N(CH3)-COO-C6H4-C6H11  (35)

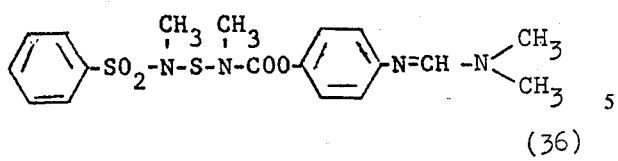 (36)

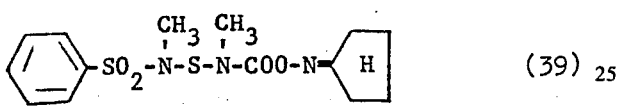 (37)

 (38)

 (39)

 (40)

and the like.

It will be appreciated that the instant specification and examples are set forth by way of illustration and not limitation, and that various modifications and changes may be made without departing from the spirit and scope of the present invention.

What is claimed is:

1. A N-sulfenylated carbamate of the formula

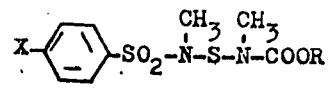

in which

X is halogen, $C_1$–$C_6$ alkyl or hydrogen, and
R is a phenyl, 2-isopropoxyphenyl, 3,5-dimethyl-4-methylmercapto-phenyl, 3-methyl-4-dimethylaminophenyl, 4-nitrophenyl, 2-allyloxyphenyl, 3-sec.-butyl-4-methylphenyl, 4-methyl-3-isopropyl-phenyl, 2-dimethylaminophenyl, or 1-naphthyl radical.

2. The compound according to claim 1 of the formula

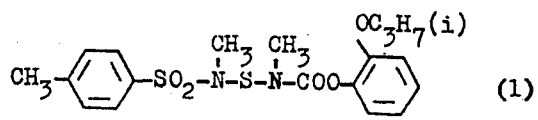 (1)

* * * * *